United States Patent [19]
DaCunha et al.

[11] Patent Number: 5,846,551
[45] Date of Patent: Dec. 8, 1998

[54] WATER-BASED MAKEUP COMPOSITIONS AND METHODS FOR THEIR PREPARATION

[75] Inventors: Kathleen DaCunha, Stamford, Conn.; Linda McKenna, North Babylon, N.Y.; David Chant, Bayport, N.Y.; Deborah Jennings, Huntington, N.Y.

[73] Assignee: E-L Management Corp., New York, N.Y.

[21] Appl. No.: 661,250

[22] Filed: Jun. 10, 1996

[51] Int. Cl.$^6$ .................................................. A61K 9/00
[52] U.S. Cl. ........................ 424/401; 424/63; 424/450; 424/489; 424/490; 424/78.03
[58] Field of Search .............................. 424/63, 401, 450, 424/489, 490, 78.03

[56] References Cited

U.S. PATENT DOCUMENTS

| | | | |
|---|---|---|---|
| 4,622,074 | 11/1986 | Miyoshi et al. | 106/308 |
| 4,853,228 | 8/1989 | Wallach et al. | 424/450 |
| 4,855,090 | 8/1989 | Wallach | 264/4.1 |
| 4,895,452 | 1/1990 | Yiournas et al. | 366/173 |
| 4,911,928 | 3/1990 | Wallach | 424/450 |
| 4,917,951 | 4/1990 | Wallach | 428/402.2 |
| 4,942,038 | 7/1990 | Wallach | 424/450 |
| 5,013,497 | 5/1991 | Yiournas et al. | 264/4.1 |
| 5,019,174 | 5/1991 | Wallach | 134/40 |
| 5,023,086 | 6/1991 | Wallach | 424/450 |
| 5,032,457 | 7/1991 | Wallach | 428/402.2 |
| 5,104,736 | 4/1992 | Wallach | 428/402.2 |
| 5,147,723 | 9/1992 | Wallach | 428/402.2 |
| 5,160,669 | 11/1992 | Wallach et al. | 264/4.3 |
| 5,164,191 | 11/1992 | Tabibi et al. | |
| 5,213,805 | 5/1993 | Wallach et al. | 424/450 |
| 5,234,767 | 8/1993 | Wallach | 428/402.2 |
| 5,256,422 | 10/1993 | Albert et al. | 424/450 |
| 5,260,065 | 11/1993 | Mathur et al. | 424/450 |
| 5,474,848 | 12/1995 | Wallach | 428/402.2 |
| 5,520,917 | 5/1996 | Mizuguchi et al. | 424/401 |
| 5,560,917 | 10/1996 | Cohen et al. | 424/401 |
| 5,658,555 | 8/1997 | Ascione et al. | 424/59 |
| 5,660,839 | 8/1997 | Allec et al. | 424/401 |

FOREIGN PATENT DOCUMENTS

WO 94/15580  7/1994  WIPO.

Primary Examiner—S. Mark Clardy
Assistant Examiner—Michael A. Williamson
Attorney, Agent, or Firm—Karen A. Lowney, Esq.

[57] ABSTRACT

Water-based makeup compositions and methods for their preparation are disclosed. The compositions comprise a water-dispersible pigment having a nonionic coating, a lipid vesicle comprising one or more lipid components, and a cosmetically or pharmaceutically acceptable aqueous carrier, and possess unusual stability at low pH. A method for the preparation of such water-based makeup compositions is disclosed as well.

25 Claims, No Drawings

WATER-BASED MAKEUP COMPOSITIONS AND METHODS FOR THEIR PREPARATION

FIELD OF THE INVENTION

The present invention relates generally to makeup compositions. More specifically, the invention relates to water-based makeup compositions comprising a water-dispersible pigment having a nonionic coating, a lipid vesicle comprising one or more lipid components, and a cosmetically or pharmaceutically acceptable aqueous carrier. The invention additionally relates to methods for the preparation of such compositions. The compositions possess unusual stability at low pH.

BACKGROUND OF THE INVENTION

The modern cosmetic chemist is often required to choose between two conflicting goals when formulating water-based makeup products: On the one hand, there is an increasing demand by consumers for water-based compositions adjusted to the skin's native acidic pH of 5–6. One the other hand, the use of uncoated and/or otherwise unmodified metallic oxide pigments in water-based makeup compositions dictates that such compositions be formulated using high levels of surfactants, and at a pH of 6.5 or greater, to prevent substantial agglomeration of the pigments from occurring over time. Such agglomeration is believed to occur as a result of attractive interactions between surface charges on the naked metal oxide particles.

A further difficulty in the formulation of water-based makeup compositions is that they should desirably comprise one or more lipid vesicles to enhance their skin-compatibility characteristics. Such lipid vesicles have been shown to be useful both as skin moisturizing agents in their own right, as well as efficient vehicles for the delivery of a variety of dermatologically active materials into the skin. However, lipid vesicles are rapidly degraded in the presence of the high concentrations of surfactants needed to properly disperse uncoated and/or unmodified metallic oxide pigments in water-based makeup compositions.

Hydrophobically-coated pigments which are less prone towards agglomeration have been prepared; see, for example Jorgensen, International Application Publication No. WO 94/15580. However, these pigments are not readily water-dispersible and as a result are generally unsuitable for use with water-based compositions.

There is therefore an ongoing need to develop novel water-based makeup compositions which are stable at acidic pH values. There is also a need to develop water-based makeup compositions which are compatible with the presence of lipid vesicles.

SUMMARY OF THE INVENTION

It is an object of the present invention to provide novel water-based makeup compositions. It is a further object of this invention to provide water-based makeup compositions which are stable at acidic pH values. It is a still further object of this invention to provide water-based makeup compositions which are compatible with the presence of lipid vesicles. It is a yet further object of this invention to provide a method for the preparation of such compositions.

These and other objects of the present invention are achieved by providing water-based makeup compositions which comprise:

(a) a water-dispersible pigment having a nonionic coating;

(b) a lipid vesicle comprising one or more lipid components; and (c) a cosmetically or pharmaceutically acceptable aqueous carrier.

In accordance with the present invention there is additionally disclosed a method for the preparation of water-based makeup compositions comprising blending a water-dispersible pigment having a nonionic coating with a lipid vesicle comprising one or more lipid components in a cosmetically or pharmaceutically acceptable aqueous carrier.

The water-based makeup compositions of the present invention are stable against both physical and chemical degradation during extended storage, over a wide temperature range. They are aesthetically elegant and non-irritating upon application to the skin, and are particularly useful in the preparation of foundation, blush, mascara and eye makeup products.

DETAILED DESCRIPTION OF THE INVENTION

As mentioned hereinabove, a first essential ingredient of the compositions of the present invention is a water-dispersible pigment having a nonionic coating. The pigment is present in the composition preferably in an amount of 0.1 to about 40 percent by weight of the total composition, and more preferably in an amount of from about 0.1 to about 20 percent by weight of the total composition. In a preferred embodiment the pigment has an average particle diameter of less than 10 microns, most preferably about one micron.

The term "water-dispersible pigment" for purposes of the present invention refers to any pigment which may be readily dispersed within an aqueous vehicle by blending the pigment and vehicle together at room temperature, without the use of high levels of surfactants, and once so dispersed is not prone towards agglomeration or clumping in the composition, even when the composition is subjected to wide variations in temperature and/or pH.

The term "nonionic coating" for purposes of the present invention refers to any water-dispersible, substantially uncharged material which is used to essentially or substantially coat the pigment, such that the resultant coated pigment is water-dispersible as defined hereinabove. In a preferred embodiment the nonionic coating comprises a water-dispersible polymer, especially a water-dispersible silicone polymer, most especially dimethicone copolyol.

Water-dispersible pigments having an average particle diameter of about one micron, and having a nonionic coating comprised of dimethicone copolyol are available commercially from Creative Polymers, Inc., Kendall Park, N.J., as Hydrophobic Pigment A 8110 (titanium dioxide), Hydrophobic Pigment A 1226 (red iron oxide), and Hydrophobic Pigment A 1405 (black iron oxide).

A second essential ingredient of the compositions of the present invention is a lipid vesicle. The term "lipid vesicle" for purposes of the present invention refers to any spherical, self-closed structure composed of one or more lipid components arranged in the form of curved lipid bilayers which entrap part of the solvent in which they freely float. Such lipid vesicles, also referred to as liposomes, may consist of one or several concentric membranes; their size ranges from 20 nanometers to several dozen micrometers, while the thickness of the membrane is around 4 nanometers. For a more detailed discussion of lipid vesicles, see D.D. Lasc, "Liposomes, From Physics To Applications," (Elsevier, N.Y., 1993), which is incorporated herein by reference.

Especially preferred for purposes of the present invention are paucilamellar lipid vesicles comprising a nonphospholipid lipid component; see, for example: Wallach, U.S. Pat. No. 5,474,848; Mathur et al., U.S. Pat. No. 5,260,065; Albert et al., U.S. Pat. No. 5,256,422; Wallach, U.S. Pat. No. 5,234,767; Mathur et al., U.S. Pat. No. 5,213,805; Chang et al., U.S. Pat. No. 5,164,191; Mathur et al., U.S. Pat. No. 5,160,669; Wallach, U.S. Pat. No. 5,147,723; Wallach, U.S. Pat. No. 5,104,736; Wallach, U.S. Pat. No. 5,032,457; Wallach, U.S. Pat.No. 5,023,086; Wallach, U.S. Pat.No. 5,019,174; Wallach, U.S. Pat. No. 5,013,497; Wallach, U.S. Pat. No. 4,942,038; Wallach, U.S. Pat. No. 4,917,951; Wallach, U.S. Pat. No. 4,911,928; Wallach et al., U.S. Pat. No. 4,895,452; Wallach, U.S. Pat. No. 4,855,090; and Philippot et al., U.S. Pat. No. 4,853,228, all incorporated herein by reference.

The lipid component is present in the compositions of the present invention preferably in an amount of 0.1 to about 80 percent by weight of the total composition, more preferably in an amount of from about 0.1 to about 20 percent by weight of the total composition, and most preferably in an amount of from about 10 to about 20 percent by weight of the total composition.

In a preferred embodiment of the present invention the nonphospholipid lipid component comprises a material selected from the group consisting of fatty acids, fatty acid esters and cholesterol. Suitable fatty acids include, but are not limited to, palmitic acid and linoleic acid. Suitable fatty acid esters include, but are not limited to, glyceryl stearate and glyceryl stearate derivatives, especially glyceryl stearate. In an especially preferred embodiment the nonphospholipid lipid component comprises a mixture of palmitic acid, linoleic acid, glyceryl stearate and cholesterol.

A third essential ingredient of the compositions of the present invention is a cosmetically or pharmaceutically acceptable aqueous carrier. The term "cosmetically or pharmaceutically acceptable" as used herein refers to materials that are not known to be harmful to humans. These materials can be found for example in the CTFA International Dictionary of Cosmetic Ingredients as well as the U.S. Pharmacopoeia or equivalent sources. Suitable cosmetically or pharmaceutically acceptable aqueous carriers include, but are not limited to: water; glycols, such as propylene glycol and butylene glycol; and polyols, such as glycerine.

Various other optional ingredients may be included in the compositions of the present invention, including but not limited to oils, emulsifiers, stabilizers, preservatives, emollients, volatile silicones, non-volatile silicones, antiseptics, dyes, humectants, moisturizers, fragrances, sunscreens, antioxidants, and pharmacologically active materials, as well as other classes of materials whose presence may be cosmetically, or medicinally desirable. The specific type and amount of material used will vary with the desired physical, aesthetic and pharmacological properties of the final composition, and is readily determined by the skilled artisan.

In a preferred embodiment of the present invention the compositions further comprise a gellant. Preferred as a gellant is a polar gellant, especially a polar gellant comprising polyacrylamide. One such polyacrylamide gellant is available commercially under the tradename Sepigel 305 from Sepic, Inc. (Fairfield, N.J.).

In a preferred embodiment of the present invention the compositions further comprise a polyurethane. Especially preferred as a polyurethane is a polyurethane comprising trimethylol hexalactone crosspolymer available commercially under the tradename BPD-500 from Kobo Products, Inc., South Plainfield, N.J.

In yet another preferred embodiment of the invention the compositions comprise one or more sunscreens. The term "sunscreen" as used herein refers to any material which is capable of protecting human skin from ultraviolet radiation having a wavelength of from about 280 to about 400 nm, by effectively absorbing such radiation, and/or reflecting or scattering such radiation away from the surface of the skin.

Suitable sunscreens include, but are not limited to: inorganic sunscreens, such as titanium dioxide and zinc oxide; organic sunscreens, such as 2-ethylhexyl p-methoxycinnamate; and mixtures thereof.

In yet another preferred embodiment of the invention the compositions include one or more pharmacologically active materials. Especially preferred as pharmacologically active material are dermatologically active materials including, but not limited to: vitamins, such as vitamin E and vitamin E acetate; antiperspirant agents; antiacne agents; antidandruff agents; antifungal agents; antiinflammatory agents; and mixtures thereof.

As mentioned hereinabove, a particularly useful feature of the compositions of the present invention is that they are stable at acidic pH ranges. Preferably the compositions are formulated at a pH of between 3 and 8.5, most preferably at a pH of between 3 and 5.5.

In a preferred embodiment the pH is adjusted by the addition of one or more buffers to the compositions. Preferably the buffer is an organic acid and/or one or more of its corresponding salts, especially an alpha-hydroxyacid and/or one or more of its corresponding salts. Suitable buffers include, but are not limited to: lactic acid, glycolic acid, citric acid, alpha-hydroxyoctanoic acid, alpha-hydroxydecanoic acid, alpha-hydroxylauric acid, tartaric acid, glucouronic acid, galactouronic acid, alpha-hydroxybutyric acid, alpha-hydroxyisobutyric acid, malic acid, mandelic acid, pyruvic acid, tartronic acid and/or one or more of their corresponding salts, and mixtures thereof. In an especially preferred embodiment the buffer is a combination of citric acid and sodium citrate.

In accordance with the present invention there is additionally disclosed a method for the preparation of a water-based makeup composition comprising blending a water-dispersible pigment having a nonionic coating with a lipid vesicle comprising one or more lipid components in a cosmetically or pharmaceutically acceptable aqueous carrier. The term "blending" for purposes of the present invention includes, but is not limited to, combining with the aid of a high-energy mixer such as a Silverson homogenizer and the like.

The following non-limiting example illustrates various embodiments of the present invention:

WATER-BASED MAKEUP COMPOSITION

| Ingredient | Percent by Weight |
| --- | --- |
| Phase 1 | |
| Purified Water | 32.98 |
| Cholesterol | 2.10 |
| Glyceryl Stearate | 9.75 |
| Linoleic Acid | 0.43 |
| Palmitic Acid | 0.43 |
| Phase 2 | |
| Hydrophobic Pigment A 8110 | 9.50 |
| Butylene Glycol | 4.20 |
| Cyclomethicone | 7.14 |

-continued

WATER-BASED MAKEUP COMPOSITION

| Ingredient | Percent by Weight |
| --- | --- |
| Dimethicone | 9.69 |
| BPD-500 | 5.00 |
| Purified Water | 17.25 |
| Sepigel 305 | 1.00 |
| Citric Acid | 0.15 |
| Sodium Citrate | 0.38 |

PROCEDURE

1. Phase 1 ingredients are combined according to Wallach (vide supra, incorporated patents) to provide a lipid vesicle-containing mixture. This mixture is then blended with the ingredients of Phase 2 at a temperature of not more than 35° C. to provide a stable, elegant, low-pH, water-based makeup composition.

While the present invention has been set forth in terms of specific embodiments thereof, it will be understood that numerous variations are now enabled to those skilled in the art. Accordingly, the invention is to be broadly construed and limited only by the scope of the appended claims.

What is claimed is:

1. A water-based makeup composition stable at an acidic pH range which comprises:
   (a) a water-dispersible metallic oxide having a nonionic coating in an amount of from about 0.1 to about 40 percent by weight of total composition;
   (b) a lipid vesicle comprising one or more lipid components in an amount of from about 0.1 to 80 percent by weight of total composition; and
   (c) a cosmetically or pharmaceutically acceptable aqueous carrier.

2. The composition of claim 1 wherein the pigment is present in an amount of from about 0.1 to about 20 percent by weight of the total composition.

3. The composition of claim 1 wherein the pigment has an average particle diameter of less than about 10 microns.

4. The composition of claim 1 wherein the pigment has an average particle diameter of about 1 micron.

5. The composition of claim 1 wherein the coating comprises a water-dispersible polymer.

6. The composition of claim 5 wherein the water-dispersible polymer is a water-dispersible silicone polymer.

7. The composition of claim 6 wherein the silicone polymer comprises dimethicone copolyol.

8. The composition of claim 1 wherein the lipid vesicle is a paucilamellar lipid vesicle.

9. The composition of claim 1 wherein the lipid vesicle comprises at least one phospholipid lipid component.

10. The composition of claim 8 wherein the lipid vesicle comprises at least one nonphospholipid lipid component.

11. The composition of claim 1 wherein the lipid component is present in an amount of from about 10 to about 20 percent by weight of the total composition.

12. The composition of claim 10 wherein the nonphospholipid lipid component is selected from the group consisting of fatty acids, fatty acid esters and cholesterol.

13. The composition of claim 12 wherein the fatty acid is selected from the group consisting of palmitic acid and linoleic acid.

14. The composition of claim 12 wherein the fatty acid ester is selected from the group consisting of glyceryl stearate and glyceryl stearate derivatives.

15. The composition of claim 14 wherein the fatty acid ester is glyceryl stearate.

16. The composition of claim 1 having a pH of between 3 and 8.5.

17. The composition of claim 16 having a pH of between 3 and 5.5.

18. The composition of claim 1 further comprising a gellant.

19. The composition of claim 18 wherein the gellant is a polar gellant.

20. The composition of claim 19 wherein the polar gellant comprises a polyacrylamide.

21. The composition of claim 1 further comprising a polyurethane.

22. The composition of claim 21 wherein the polyurethane comprises a trimethylol hexalactone crosspolymer.

23. A water-based makeup composition stable at an acid c pH range which comprises:
   (a) a water-dispersible metallic oxide pigment having a nonionic coating in an amount of from about 0.1 to about 40 percent by weight of total composition, wherein the nonionic coating comprises dimethicone copolyol;
   (b) a lipid vesicle comprising one or more lipid components in an amount of from about 0.1 to 80 percent by weight of total composition;
   (c) a gellant;
   (d) a polyurethane; and
   (e) a cosmetically or pharmaceutically acceptable aqueous carrier.

24. The composition of claim 23 wherein the lipid vesicle comprises at least one nonphospholipid component and the gellant is a polar gellant.

25. A method for the preparation of a water-based makeup compositions stable at an acidic pH range comprising blending a water-dispersible metallic oxide pigment having a nonionic coating in an amount of from about 0.1 to about 40 percent by weight of total composition with a lipid vesicle in an amount of from about 0.1 to 80 percent by weight of total composition comprising one or more lipid components in a cosmetically or pharmaceutically acceptable aqueous carrier.

* * * * *